(12) United States Patent  
Mazda et al.

(10) Patent No.: US 7,131,972 B2
(45) Date of Patent: Nov. 7, 2006

(54) VERTEBRAL FIXING DEVICE

(75) Inventors: Keyvan Mazda, Paris (FR); Régis Le Couedic, Andresy (FR)

(73) Assignee: Abbott Spine, Bordeaux (FR)

( * ) Notice: Subject to any disclaimer, the term of this patent is extended or adjusted under 35 U.S.C. 154(b) by 268 days.

(21) Appl. No.: 10/489,158

(22) PCT Filed: Sep. 25, 2002

(86) PCT No.: PCT/FR02/03263

§ 371 (c)(1),
(2), (4) Date: Mar. 9, 2004

(87) PCT Pub. No.: WO03/026521

PCT Pub. Date: Apr. 3, 2003

(65) Prior Publication Data

US 2004/0267259 A1 Dec. 30, 2004

(30) Foreign Application Priority Data

Sep. 26, 2001 (FR) .................................. 01 12354

(51) Int. Cl.
*A61B 17/70* (2006.01)
(52) U.S. Cl. ....................................................... 606/61
(58) Field of Classification Search .................. 606/61, 606/69–72

See application file for complete search history.

(56) References Cited

U.S. PATENT DOCUMENTS

| | | | |
|---|---|---|---|
| 4,003,376 A | | 1/1977 | McKay et al. |
| 5,330,473 A | * | 7/1994 | Howland ..................... 606/61 |
| 5,360,431 A | * | 11/1994 | Puno et al. ................... 606/72 |
| 5,397,363 A | * | 3/1995 | Gelbard ........................ 606/61 |
| 5,688,272 A | * | 11/1997 | Montague et al. ............ 606/61 |
| 5,928,232 A | | 7/1999 | Howland et al. |
| 6,277,120 B1 | * | 8/2001 | Lawson ......................... 606/61 |

* cited by examiner

Primary Examiner—Eduardo C. Robert
Assistant Examiner—Richard Shaffer
(74) Attorney, Agent, or Firm—Dennis G. LaPointe

(57) ABSTRACT

A vertebral fixing device which is capable of being mounted on a vertebra having a rear wall and/or two side walls from which project the ribs and/or the transverse processes. The device comprises an elongate transverse part (16) having two substantially symmetrical opposite ends (18, 20), where the transverse part (16) is adapted to be arranged against the rear wall (51) of the vertebra. Each of the ends (18, 20) is located opposite one rib and/or a transverse process (52, 54). The device includes at least two clamp-forming adjustable connection elements (26, 28, 42, 44) suitable for being connected respectively to each of the two ends (18, 20). The ribs and/or transverse processes (52, 54) are adapted to be engaged in the adjustable connection elements (26, 28, 42, 44) so as to maintain the elongate transverse part (16) in a fixed position against the rear wall (51) of the vertebra.

11 Claims, 4 Drawing Sheets

VERTEBRAL FIXING DEVICE

RELATED APPLICATION

This application is a national stage application under 35 USC 371 of international application PCT/FR02/03263 filed Sep. 25, 2002, which in turn claims the priority benefit of France application FR 01/12354 filed Sep. 26, 2001.

The present invention relates to a vertebral fixing device suitable for being mounted on a vertebra, and to an assembly for straightening the spine using such a device.

FIELD OF THE INVENTION

The intended field of application is particularly, but not exclusively, the treatment of scoliosis, or more generally correcting abnormal curvature of the spine.

BACKGROUND OF THE INVENTION

The spine is formed by superposed vertebrae, that are normally in alignment along a vertical axis, from the lumbar vertebrae to the cervical vertebrae, each vertebra presenting a posterior wall from which there projects a spinous process and presenting two sides having walls from which there project ribs and/or transverse processes. When the spine of an individual presents abnormal curvature, the vertebrae are inclined relative to one another and relative to said vertebral axis. The sides of the vertebrae situated on one side are thus moved towards each other so as to form a concave side, whereas the sides of the vertebrae on the other side are moved apart from each other so as to form a convex side.

In order to straighten the vertebral column, the sides of the vertebrae on the concave side need to be moved further apart so as to be situated relative to one another at a distance that is substantially equivalent to the distance between the sides of the vertebrae on the other side. In order subsequently to hold the vertebrae relative to one another, known devices have screws that are inserted into the vertebrae or hooks that are inserted along the inside wall of the spinal canal and rods for interconnecting the screws or the hooks.

The hooks are generally inserted in pairs into each vertebra and from either side close to the pedicles, their heads projecting from the posterior wall of the vertebra, one on either side of the spinous process. The heads form sockets, for example, suitable for receiving a rod which is locked in position by means of a nut screwed onto the head and bearing against the rod. The rows constituted by the heads of the hooks situated on either side of the spinous processes are interconnected and held in a fixed position by two rods that are parallel to each other and to the axis of the spine.

Nevertheless, hooks are difficult to use since the operator must under no circumstances harm the spinal cord which occupies the center of the spinal canal, since otherwise the patient will be paralyzed.

The use of screws makes it possible to reduce the risks of such surgery. The screws likewise present socket-forming heads and are inserted in pairs into the posterior walls of the vertebrae in the pedicles on either side of the spinous processes. Thus, the screws constitute fixing points in the vertebrae for holding them relative to one another. Nevertheless, they are necessarily inserted into the pedicles of the vertebrae which can, in some circumstances, be small in size or easily damaged.

SUMMARY OF THE INVENTION

A problem which arises and which the present invention seeks to solve is to provide fixing points when it is not possible to introduce screws into the vertebrae of the curved portion and when the use of hooks is too dangerous.

To achieve this object, in a first aspect, the present invention provides a transverse part of elongate shape presenting two opposite ends that are substantially symmetrical to each other about a plane of symmetry intersecting said elongate transverse part orthogonally, each end presenting a first main face, a second main face, and an end edge face, said part being suitable for being placed against said posterior wall of said vertebra substantially perpendicularly to the axis of said vertebral column, each of the first main faces of said ends being situated facing a rib and/or a transverse process; at least two adjustable connection elements forming clamps, suitable for being connected respectively to each of said two ends facing said first main face and spaced apart from each other, said ribs and/or transverse processes being suitable for being engaged in said adjustable connection elements in such a manner as to hold said transverse part in a fixed position against said posterior wall of said vertebra; and said device includes anchor means situated in said ends of said transverse part on which the connection members are Suitable for being mounted in order to displace said vertebra.

Thus, a characteristic of the vertebral fixing device lies in the way in which fixing points are made on each of the vertebrae of the spine by means of transverse parts which are secured to each vertebra. These transverse parts are not fixed to the vertebrae by means of screws, but by means of two adjustable connection elements each, connecting their ends to the transverse processes and/or the ribs situated on either side of the vertebrae. As a result, the anchor means can be mounted on the ends of transverse parts secured to a sequence of vertebrae that are to be displaced, and they can be held in fixed position relative to one another by means of two rods, one on either side of the spinous processes, and fixing systems which unite them securely to the rod portions.

In a particularly advantageous embodiment of the invention, each of said adjustable connection elements comprises a U-shaped part whose spaced-apart limbs have free ends that are provided with connection means and adjustment means suitable for co-operating with said ends of said transverse part. As a result, for each of the two sides of a vertebra, the U-shaped part is engaged on the transverse process and/or the rib that projects from the side wall of the vertebra so that the bottom of the U-shaped part bears against the anterior wall of the process or the rib and so that the limbs are directed substantially in the same direction as the spinous processes. The two U-shaped parts are then connected to the two ends of an elongate transverse part by the connection means and the adjustment situated on the free ends of the limbs.

In a particular embodiment, said U-shaped part is made of a deformable material suitable for pressing against the outlines of said ribs and/or transverse processes engaged in said U-shaped part. Thus, the U-shaped part presents points of contact all around the ribs or the processes, thereby ensuring better fastening thereto.

Preferably, each of said ends of said transverse part presents at least two recesses opening out respectively at least into said first and second main faces of said ends and situated relative to each other substantially perpendicularly to said transverse part, said recesses being suitable for co-operating with adjustable connection elements. Thus, as explained in greater detail in the description below, the adjustable connection elements are connected in simplified manner to the transverse part by means of the recesses that go through its ends.

In a particularly advantageous embodiment of the invention, at least one of the two recesses opens out into the end edge face of said end in the direction facing away from the other recess. Thus, as also explained in greater detail in the description below, this disposition makes it possible in a particular embodiment of the invention to mount the transverse parts on the vertebrae in simplified and rapid manner.

Advantageously, said free ends of said limbs of said U-shaped part are suitable for being inserted freely in said recesses facing said first main face, said connection means and said adjustment means secured to said free ends being suitable for bearing against said second main face to prevent said U-shaped part from moving in translation away from said first main face and for moving at least one of said limbs in translation towards said first main face. Thus, when the transverse part bears against the posterior wall of the vertebra and the two U-shaped parts situated on either side of the vertebra, engaged behind the transverse processes or the ribs and bearing against them, and when the free ends of the limbs of each U-shaped part are inserted in the corresponding recesses, using said adjustment means enables said transverse part to be fixed in position against the vertebra.

In a first particular embodiment of the invention, said connection means are formed by shoulder-forming means at the free end of the limb of the U-shaped part, the free end of the other limb having the adjustment means. Thus, said shoulder is suitable for bearing against the second main face in such a manner as to prevent said limb from moving in translation away from said first main face, the bottom of the U-shaped part coming to bear against the anterior wall of the rib or the transverse process, while the free end of the other limb carries the adjustment means. As a result, actuating the adjustment means enables the limb on which they are mounted to be entrained towards the first main face, thereby causing the U-shaped part to pivot about the bearing point of the shoulder, consequently causing the bottom of the U-shaped part to move towards the first main face and thus clamp against the rib and/or the process. Naturally, in this first particular embodiment of the invention, the two limbs must be spaced far enough apart from each other to obtain clearance between the U-shaped part and the ribs or the process so as to allow pivoting to take place without difficulty.

In particularly advantageous manner, said free ends of said limbs present thread-forming means suitable for having a nut screwed thereon to form said connection means and said adjustment means. Thus, the nut is suitable for being turned about the free end of the corresponding limb, thereby causing the bottom of the U-shaped part to be displaced when applying clamping. As a result, the nut bearing against the second main face around the recess through which the free end of the limb passes causes the U-shaped part to be moved towards the first main face opposite from the second main face.

In a particular embodiment of the invention, said anchor means are secured to said main faces of said ends and project substantially perpendicularly to said second main faces. As a result, the anchor means extend in a direction away from the posterior wall of the vertebra into an empty space that a fixing system can occupy.

In another particular embodiment of the invention, said anchor means extend said adjustable connection elements where they face said second main faces. Thus, the anchor means likewise extend away from the posterior wall of the vertebra, but they are secured to adjustable connection elements, thereby reducing the number of operations to be performed when mounting the transverse part itself and making it possible to obtain a vertebral fixing device of greater strength for a given quantity of material.

In a second aspect, the present invention provides an assembly for straightening the spine, the assembly comprising a plurality of vertebral fixing devices in accordance with the invention mounted on a plurality of successive vertebrae, said anchor means forming substantially two rows situated on either side of the row of spinous processes of said plurality of vertebrae; fixing systems mounted on each of the anchor means and suitable for receiving a rod, each of said devices being suitable for holding the anchor means and the rod in a fixed position relative to each other; and two longitudinal rods interconnecting said devices in each of said rows respectively of the anchor means on either side of said row of spinous processes, thereby holding the anchor points of a given row in fixed positions, at least relative to one another.

BRIEF DESCRIPTION OF THE DRAWINGS

Other features and advantages of the invention appear better on reading the following description of particular embodiments of the invention given by way of non-limiting indication and with reference to the accompanying drawings, in which.

DETAILED DESCRIPTION OF THE INVENTION

Figure 1:
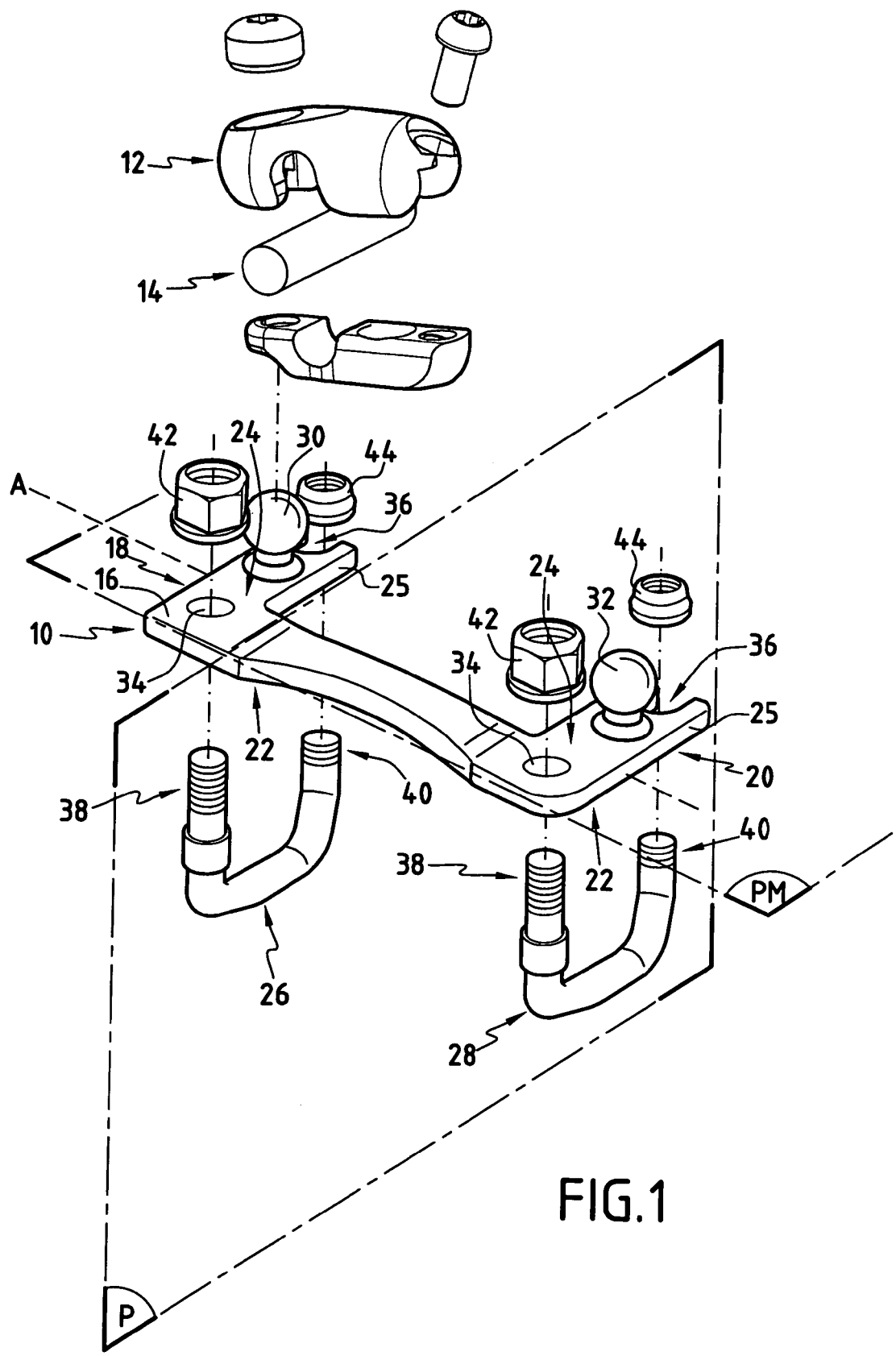
FIG. 1 is an exploded view showing a first embodiment of a fixing device in accordance with the invention.
Figure 2:
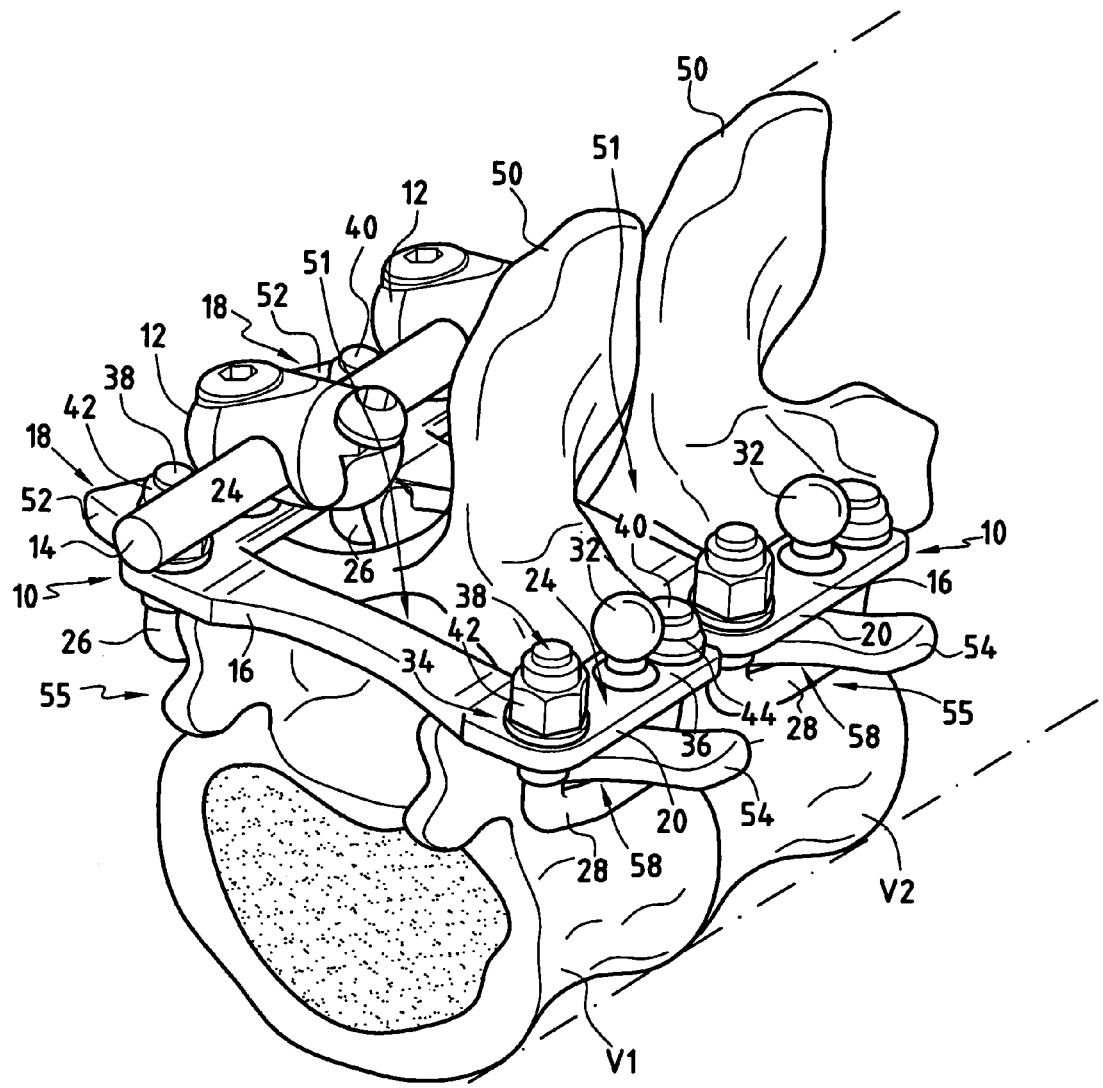
FIG. 2 is a perspective view showing a portion of spine comprising two vertebrae fitted with two vertebral fixing devices as shown in FIG. 1.

Reference is made to FIGS. 1 and 2 for describing a first embodiment of a vertebral fixing device.

FIG. 1 shows a vertebral fixing device 10 in accordance with the invention and suitable for receiving at least one fixing system 12 enabling a rod 14 to be held in a fixed position, with only a portion of the rod being shown in the figure.

The vertebral fixing device 10 includes a transverse elongate part 16 of axis A defining a mean plane Pm and presenting two opposite ends 18, 20. These two ends 18, 20 are substantially images of each other about a plane of symmetry P which intersects the transverse part 16 orthogonally; each presents a first main face 22 and a second main face 24, together with an end edge 25. Facing the two main faces 22, two adjustable connection elements 26 and 28 are suitable for being connected to the respective ends 18 and 20. In addition, the ends have respective anchor means 30 and 32 of spherical shape projecting from their second main faces 24.

To make a connection, the ends 18 and 20 present respective first recesses 34 constituted by respective holes, and second recesses 36 opening out into the edge face 25 looking away from the first recesses 34. The first and second recesses are spaced apart from each other by a first distance and they pass through the transverse part 16 so as to open out in the first and second main faces 22 and 24. In addition, the first and second holes 34 and 36 define a line that is substantially perpendicular to the transverse part 16.

Each of the connection elements 26 and 28 is in the form of a U-shaped part with the free ends 38 and 40 of its two limbs being spaced apart from each other by a distance corresponding to said first distance, and threaded so as to be capable of receiving nuts 42 and 44. It will be understood that the free ends 38 and 40 of the limbs are for insertion into the recesses 34 and 36 with the connection elements 26 and 28 coming respectively into register with the first main faces 22 of the transverse part 16. Once the free ends 38 and 40 have been inserted through the recesses 34 and 36 so as to project from the second main face 24, the nuts 42 and 44 can be screwed onto them in order to retain the connection parts, and as described in greater detail in the description below, in order to prevent the transverse part 16 from moving relative to the posterior wall of the vertebra.

The shape of the second recess 36 makes it easier to mount the connection elements 26 and 28 on the transverse part, and in particular makes mounting quicker, said second recess opening out into the edge face 25 and forming an oblong hole. Thus, when the transverse part 16 is in the installation position, the nuts 44 are pre-mounted on the free ends 40 of the limbs of each U-shaped part, and the part is presented in a plane parallel to the plane P, the free end 40 being directed towards the second recess 36 so that the limbs slope relative to the mean plane Pm. Thereafter, the limb of the U-shaped part presenting the free end 40 is engaged substantially parallel to the mean plane Pm in the recess 36 so that the nut 44 comes to bear against the second face 24. This enables the U-shaped part to be pivoted about the point where the nut 44 bears against the second face, so that the other free end 38 which was initially situated facing the first face 22 becomes engaged in the recess 34 and is subsequently held in place by the nut 42. As explained in the description below, when the U-shaped part pivots, it is suitable for holding captive a rib or a process situated facing the first face 22.

In a particular embodiment, the U-shaped part is deformable so that it presses snugly against the outline of an object it surrounds, thereby providing better retention. The materials used for making the U-shaped part, in this embodiment, are essentially polymers of the polyethylene type or any other biocompatible material either in raw form or worked as a braid.

Naturally, the free ends of the limbs of the deformable U-shaped part must include connection means and adjustment means that are suitable for the material. Thus, the free ends of the limbs are crimped in a rigid material element suitable for being threaded or for constituting a shoulder. In another embodiment, the elements are suitable for being overmolded on the free ends of the limbs.

As a result, the connection means and the adjustment means are secured irreversibly to the free ends of the limbs of the U-shaped part so that prolonged traction exerted on the U-shaped part by the connection means and the adjustment means does not cause them to separate.

The anchor means 30 and 32 formed by the spherical heads are situated on the second main surfaces 24, between the two recesses 34 and 36. They are securely connected to the transverse part 16, e.g. by welding, so that the mechanical forces exerted on said means 30 and 32 can move the part 16 without leading to separation.

As explained below with reference to FIG. 2, this mechanical action is performed by means of a fixing system 12 and a rod 14.

FIG. 2 shows two consecutive vertebrae V1 and V2 forming a portion of the spine, each having a spinous process 50 projecting from the posterior wall 51 and two transverse processes 52 and 54 projecting from sides 55. Each vertebra V1 and V2 is fitted with a vertebral fixing device 10 in accordance with the invention and as shown in FIG. 1. In addition, the two vertebral fixing devices 10 are connected to each other by means of two fixing systems 12 which are interconnected by the rod 14.

For reasons of clarity, only two vertebrae V1 and V2 are shown. Nevertheless, vertebral fixing devices of the invention are suitable for being mounted on several successive vertebrae. Similarly, only one rod 14 and only two fixing systems are shown, whereas in a normal configuration, fixing systems are mounted on the spherical heads 32 symmetrically about the spinous process 50 and are likewise interconnected by means of a rod.

As shown in FIG. 2, the transverse parts 16 bear against the posterior walls 51 of the vertebrae substantially perpendicularly to the axis AR of the spine. They are held in this position by means of the U-shaped parts 28 and 26 whose free ends 38 and 40 are held in the recesses 34 and 36 by means of the nuts 42 and 44 which press against the second main faces 24. It will be understood that by tightening the nuts 42 and 44 about the free ends of the limbs, the bottoms of the U-shaped parts are pulled against the anterior walls 58 of the transverse processes, and consequently the ends 18 and 20 of the transverse parts are pulled towards the transverse processes 54 and 52. As a result, the elongate transverse part 16 is held on either side of the vertebra and bears against its posterior wall. In this way it is completely prevented from moving relative to the vertebra. Naturally, the nuts must be tightened sufficiently to compress the bony wall slightly in order to guarantee good retention.

Once the vertebral fixing devices have been secured to the vertebrae, the fixing systems fitted with a rod are put into place and clamped on the spherical heads on both sides of the spine, possibly after the spine has been straightened out. Thus, the fixing systems 12 are held in a fixed position relative to the spherical heads and the rod is prevented from moving relative to the fixing systems so that the spherical heads are prevented from moving relative to one another. Consequently, the vertebrae are held laterally in positions that are fixed relative to one another.

Figure 3:
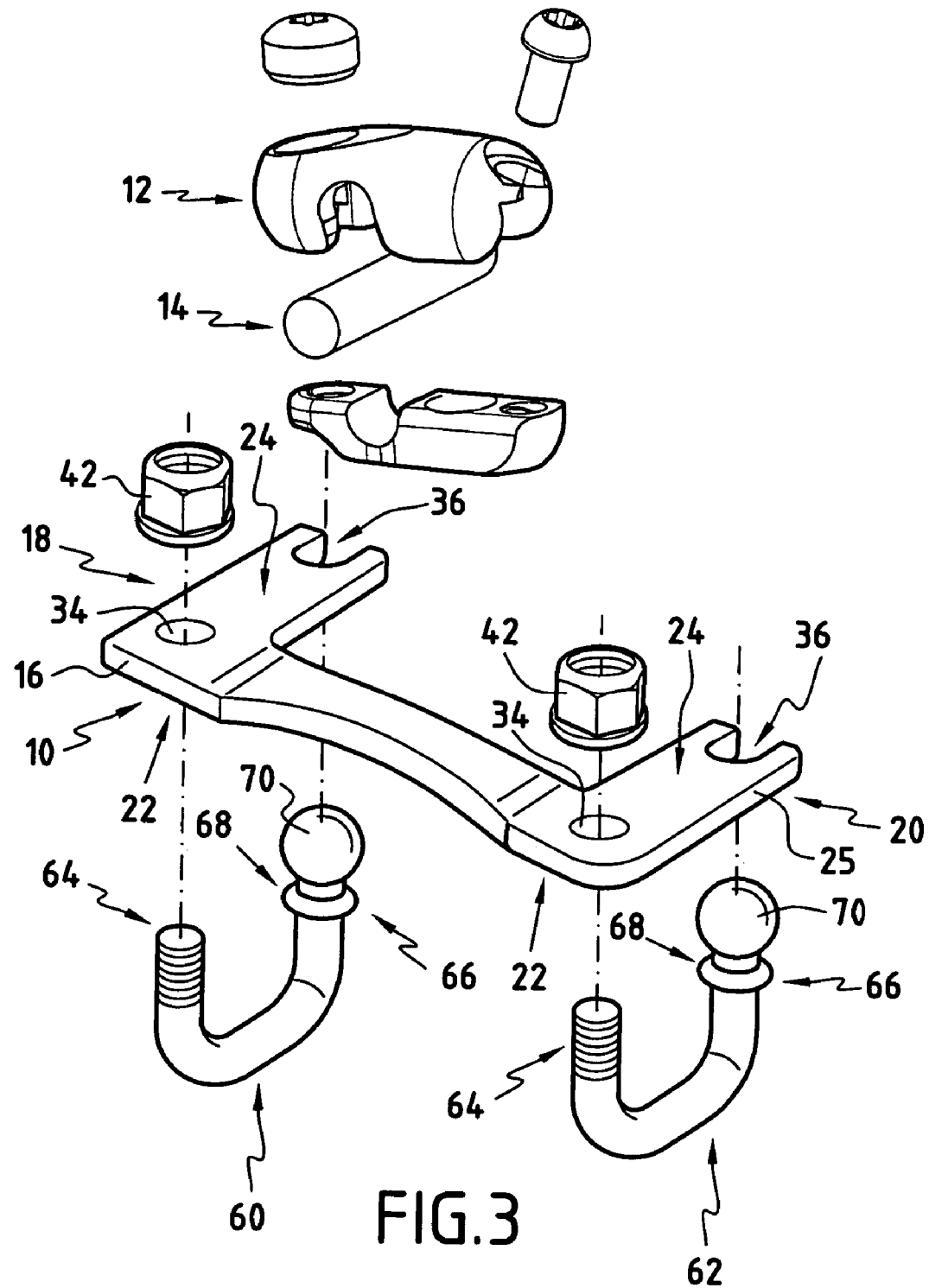
FIG. 3 is an exploded view showing a second embodiment of a vertebral fixing device in accordance with the invention.
Figure 4:
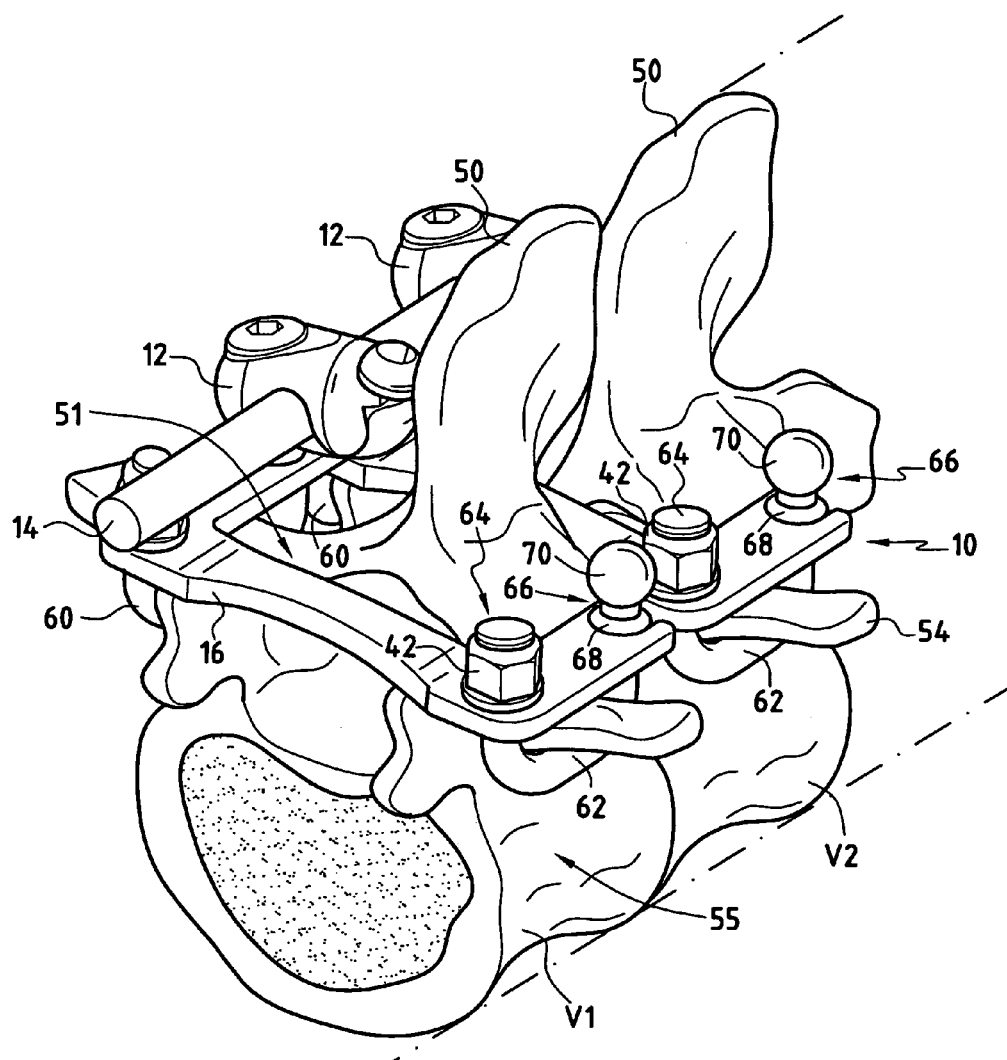
FIG. 4 is a perspective view showing a portion of spine comprising two vertebrae fitted with two vertebral fixing devices as shown in FIG. 3.

Reference is made to FIGS. 3 and 4 while describing clamp-forming adjustable connection elements in a particular embodiment in which they are connected to the anchor means.

In this embodiment, each of the U-shaped parts 60 and 62 presents a free end 64 which is threaded so as to receive the nut 42 as in the preceding embodiment; in contrast, the other free end 66 is extended by a shoulder 68 surmounted by a spherical head 70 forming the anchor means. There is thus no need to fit the transverse part with anchor means.

In addition, as for the U-shaped part of the preceding embodiment, where the nut is pre-mounted on the free end of the limb of the part, the free end 66 of each U-shaped part 60 and 62 is engaged in the recess 36 in such a manner that the shoulder 68 bears against the second main face 24 around the recess 36. The U-shaped parts 60 and 62 are thus suitable for being pivoted about the point where the shoulder 68 bears around the recess 36 against the second main surface 34, so as to enable the other end 64 of the U-shaped part to be inserted in the recess 34. As a result, when the nut 42 is tightened onto the free end 64 of the limb of each U-shaped part 60 or 62, the corresponding part is prevented from moving in translation in the direction away from the first main face 22.

Thus, and advantageously, the spherical head constituting the anchor means is mounted on the transverse part 16 together with the connection elements with which it forms an integral part. In addition to simplifying fitting of the transverse part 16 itself, this embodiment also provides anchor means that are more firmly secured to the vertebrae that they are to move.

In the embodiments described above with reference to FIGS. 2 and 4, the connection elements are engaged solely around the transverse processes since the vertebrae shown in those figures do not carry any ribs. Naturally, it would not go beyond the ambit of the invention to mount a plurality of vertebral fixing devices on a plurality of vertebrae having ribs connected thereto. This applies in particular to the dorsal vertebrae having ribs that are connected to their sides substantially in register with the anterior walls of the transverse processes. Thus, the U-shaped part should have limbs of length greater than the limbs of the U-shaped parts used for vertebrae that do not carry ribs, and these longer parts are engaged around the ribs so that their bottoms bear against the anterior walls of the ribs and so that, as in the preceding embodiments, the free ends of the limbs pass through the recesses of the transverse part in order to be secured thereto. As a result, it will be understood that the limbs of the U-shaped part extend on either side of the transverse process, but no longer constitute an element for engaging the vertebral fixing device.

It would not go beyond the ambit of the invention to use U-shaped parts of deformable material for connecting the elongate transverse parts to vertebrae by means of ribs. Similarly, the length of the U-shaped part made of deformable material would need to be increased.

The invention claimed is:

1. A vertebral fixing device suitable for being mounted on a vertebra of the spine, said vertebra presenting a posterior wall from which there projects a spinous process and two side walls from which there project ribs and/or transverse processes, said device comprising:
   a transverse part consisting of a single piece of elongate shape having a plane of symmetry intersecting said elongate transverse part orthogonally and two opposite end portions that are substantially symmetrical to each other about said symmetry plane, each end portion presenting a first main face, a second main face, and an end edge face, said transverse part being suitable for being placed against said posterior wall of said vertebra substantially perpendicularly to the axis AR of said spine, each of the first main faces of said end portions being situated facing a rib and/or a transverse process;
   at least two adjustable connection elements forming clamps, suitable for being connected respectively to each of said two end portions, each adjustable connection element having an elongate portion extending substantially perpendicularly to a length of the transverse part and facing said first main face of an end portion when said adjustable connection element is connected to said transverse part, wherein the rib and/or transverse process can be fixed between said first main face of the end portion and said elongate portion of one of said adjustable connection elements; and
   anchor means mounted on the second main face of each of said end portions of said transverse part on which a rod fixing system is suitable for being mounted.

2. A vertebral fixing device according to claim 1, wherein each of said adjustable connection elements comprises a U-shaped part whose spaced-apart limbs have free ends that are provided with said connection elements and adjustment means for co-operating with said end portions of said transverse part.

3. A vertebral fixing device according to claim 2, wherein said U-shaped part is made of a deformable material for pressing against the outlines of said ribs and/or transverse processes engaged in said U-shaped part.

4. A vertebral fixing device according to claim 2, wherein each of said ends of said transverse part presents at least two recesses opening out respectively at least into said first and second main faces of said ends and situated relative to each other substantially perpendicularly to said transverse part, said recesses being suitable for co-operating with said adjustable connection elements.

5. A vertebral fixing device according to claim 4, wherein at least one of said two recesses opens out into the end edge face of said end in the direction facing away from the other recess.

6. A vertebral fixing device according to claim 4, wherein said free ends of said limbs of said U-shaped part are suitable for being inserted freely in said recesses facing said first main face, said connection means and said adjustment means secured to said free ends being suitable for bearing against said second main face to prevent said U-shaped part from moving in translation away from said first main face and for moving at least one of said limbs in translation towards said first main face.

7. A vertebral fixing device according to claim 6, wherein said connection elements comprise shoulder-forming means at the free end of said limb of the U-shaped part.

8. A vertebral fixing device according to claim 6, wherein said free ends of said limbs present thread-forming means and said connection means and said adjustment means comprise a nut screwed on said thread-forming means.

9. A vertebral fixing device according to claim 1, wherein said anchor means are secured to said main faces of said ends and project substantially perpendicularly to said second main faces.

10. A vertebral fixing device according to claim 1, wherein said anchor means extend said adjustable connection elements where they face said second main faces.

11. An assembly for straightening the spine, comprising:
   a plurality of vertebral fixing devices, each device comprising:
      a transverse part consisting of a single piece of elongate shape having a plane of symmetry intersecting said elongate transverse part orthogonally and two opposite end portions ends that are substantially symmetrical to each other about said symmetry plane, each end portion presenting a first main face, a second main face, and an end edge face, said transverse part being suitable for being placed against said posterior wall of said vertebra substantially perpendicularly to the axis AR of said spine, each of the first main faces of said end portions being situated facing a rib and/or a transverse process;
      at least two adjustable connection elements forming clamps, suitable for being connected respectively to each of said two end portions, each adjustable connection element having an elongate portion extending substantially perpendicularly to a length of the transverse part and facing said first main face of an end portion when said adjustable connection element is connected to said transverse part, wherein the rib and/or transverse process can be fixed between said first main face of the end portion and said elongate portion of one of said adjustable connection elements; and anchor means mounted on the second main face of each of said end portions of said transverse part on which a rod fixing system is suitable for being mounted the plurality of vertebral fixing devices mounted on a plurality of successive vertebrae, said anchor means forming substantially two rows situated on either side of the row of spinous processes of said plurality of vertebrae;

two longitudinal rods;

fixing systems mounted on each of said anchor means and suitable for receiving said rod, each of said systems being suitable for holding one of said anchor means and one of said rods in a fixed position relative to each other; and said rods interconnecting said systems in each of said rows respectively of the anchor means on either side of said row of spinous processes, thereby holding the anchor points of a given row in fixed positions, at least relative to one another.

* * * * *